United States Patent [19]

Norell

[11] 3,932,402

[45] Jan. 13, 1976

[54] PREPARATION OF SYM-TRIAZINES BY TRIMERIZATION OF NITRILES IN TRIFLUOROMETHANESULFONIC ACID

[75] Inventor: John R. Norell, Bartlesville, Okla.

[73] Assignee: Phillips Petroleum Company, Bartlesville, Okla.

[22] Filed: June 24, 1974

[21] Appl. No.: 482,257

[52] U.S. Cl. ........................................... 260/248 CS
[51] Int. Cl.² ...................................... C07D 251/24
[58] Field of Search ............................. 260/248 CS

[56] References Cited
UNITED STATES PATENTS

| | | | |
|---|---|---|---|
| 3,060,179 | 10/1962 | Toland | 260/248 |
| 3,071,586 | 1/1963 | Sandner et al. | 260/248 |
| 3,095,414 | 6/1963 | Spainhour | 260/248 |
| 3,238,138 | 3/1966 | Braunwarth et al. | 260/248 X |
| 3,654,192 | 4/1972 | Vogel | 260/2 R |

OTHER PUBLICATIONS

Cool et al., J. Chem. Soc., 1941, pp. 278–282.
Elderfield, "Heterocyclic Compounds", Vol. 7, Ch. 7, pp. 642, 644 and 686.
Migrdichian, "The Chemistry of Organic Cyanogen Compounds," Ch. 17, pp. 356, 357 and 367.

*Primary Examiner*—John M. Ford

[57] ABSTRACT

Aliphatic and aromatic nitriles are trimerized to substituted symmetrical triazines in the presence of trifluoromethanesulfonic acid.

16 Claims, No Drawings

PREPARATION OF SYM-TRIAZINES BY TRIMERIZATION OF NITRILES IN TRIFLUOROMETHANESULFONIC ACID

This invention relates to substituted sym-triazines. In one aspect it relates to the preparation of alkyl-substituted sym-triazines. In another aspect it relates to the preparation of aromatic-substituted sym-triazines.

Compounds having the sym-triazine ring structure are well known in the art as intermediates in the preparation of dyes, pharmaceuticals, rodenticides and the like. There are several processes reported in the prior art for the preparation of alkyl- and aryl-substituted triazines which require the use of various catalysts. These include strong acid catalysts such as sulfuric acid, chlorosulfonic acid, hydrochloric acid in alcohol, and Lewis acids, amides and hydrides of alkali metals and alkaline earth metals, metal alkyls, metallic sodium and elemental bromine. In the acid-catalyzed reactions, the available literature stresses that those nitriles possessing an alpha-hydrogen; i.e., aliphatic nitriles, will not trimerize. Aliphatic-substituted triazines have been prepared from aliphatic nitriles via the imidate, however, the reaction is difficult to handle and requires isolation of the imidate salt.

It is an object of this invention to provide an improved process for the preparation of substituted sym-triazines.

It is another object to provide an improved process for the preparation of alkyl-substituted sym-triazines.

It is another object to provide an improved process for the preparation of aromatic-substituted sym-triazines.

Other objects, aspects, and advantages of the invention will become apparent to those skilled in the art upon consideration of the accompanying disclosure.

In accordance with the present invention there is provided a process for the preparation of substituted triazines of the general formula

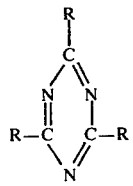

wherein R is a radical selected from the group consisting of alkyl, aryl and combinations thereof, such as aralkyl and alkaryl, and substituted aryl, such as haloaryl and alkoxyaryl, having from 2 to 9 carbon atoms per radical group, wherein the alkyl group contains an alpha-hydrogen, i.e., a hydrogen atom on the carbon atom which is bonded to the nitrile function. Substituents of the substituted aryl radical groups include halogen, alkyl and alkoxy. When present, such substituents are preferably located in the 3,4 and/or 5 positions.

According to the process of the present invention, an organic nitrile having the general formula R-CN, wherein R is selected from the group consisting of alkyl, aryl and substituted aryl having from 2 to 9 carbon atoms per radical group, wherein the alkyl group contains an alpha-hydrogen, is reacted under reaction conditions in the presence of trifluoromethanesulfonic acid to form a symmetrical triazine.

In one embodiment of this invention, the organic nitrile is an aliphatic nitrile. The product of this process is a 2,4,6-trialkyl-1,3,5-triazine.

In another embodiment of this invention, the organic nitrile is an aromatic or substituted aromatic nitrile in which case the product of the process is a 2,4,6-triaryl-1,3,5-triazine.

Examples of suitable organic nitriles for use in this invention include: propionitrile, n-butyronitrile, isobutyronitrile, n-nonanenitrile, pentanenitrile, benzonitrile, o-tolunitrile, p-chlorobenzonitrile, p-iodobenzonitrile, phenylacetonitrile, p-methoxybenzonitrile, m-fluorobenzonitrile, p-bromobenzonitrile, p-tolunitrile, m-tolunitrile and the like.

As noted above, the trimerization reaction is carried out in the presence of trifluoromethanesulfonic acid. The amount of trifluoromethanesulfonic acid used can vary within rather broad limits, ranging from 0.8 to 20 moles of trifluoromethanesulfonic acid per mole of nitrile. In a presently preferred embodiment the molar ratio of trifluoromethanesulfonic acid to nitrile is in the approximate range of 1.2 to 10.

The trimerization reaction is rapid and exothermic, therefore the admixture of nitrile and trifluoromethanesulfonic acid is prepared at relatively low temperatures to avoid overheating. After admixture of the nitrile and trifluoromethanesulfonic acid, the reaction mixture can be warmed or heated to cause the trimerization to proceed to completion. The temperature of reaction can range from $-20°$ to $100°C$, preferably from $10°$ to $50°C$. In a presently preferred embodiment, the nitrile is added to the trifluoromethanesulfonic acid.

Reaction time will be sufficient to effect the desired conversion of nitrile to triazine compound and generally ranges from 0.25 to 24 hours.

Within the parameters given above, the reaction can be carried out batchwise or continuously, using any suitable apparatus. After completion of the reaction, the trimer can be isolated and purified by any suitable means including solvent extraction, filtration, crystallization and distillation.

The present invention provides a facile process for the preparation of alkyl- and aryl-substituted triazines. Heretofore, trialkyl-substituted s-triazines were prepared either with great difficulty or not at all using the processes of the prior art.

The following examples illustrate the invention.

The exemplary runs described in the following examples were carried out in an appropriately sized 3-neck round-bottom flask equipped with a thermometer, condenser, addition funnel, nitrogen inlet tube and magnetic stirring device. According to the presently preferred procedure, the trifluoromethanesulfonic acid was placed in the reaction flask and cooled to about $0°C$. The nitrile was added, dropwise, to the cooled trifluoromethanesulfonic acid over a time period ranging from 30 minutes to 1 hour. After addition of the nitrile was complete, the reaction mixture was stirred, at room temperature, for up to about 18 hours. To isolate the trimer, the reaction mixture was poured over ice, then neutralized with ammonium hydroxide or sodium bicarbonate and the trimer isolated by filtration or by extraction with ether or methylene chloride. The trimer was purified by recrystallization or distillation.

Alternatively, most of the trifluoromethanesulfonic acid was removed from the reaction mixture by vacuum distillation prior to pouring the reaction mixture over ice. (See Example X.)

EXAMPLE I

Benzonitrile (5.2 g, 0.05 mol) was added dropwise over a period of 100 sec to 20 ml (34 g, 0.23 mol) of stirred trifluoromethanesulfonic acid with the temperature being allowed to rise as high as 91°C. When the reaction mixture cooled to 25°C, the yellow solution was poured into 100 ml cold ethanol. The yellow color disappeared and a white flocculent precipitate formed. Recrystallization of this precipitate from 150 ml chloroform afforded 3.43 g (66 percent yield) of 2,4,6-triphenyl-s-triazine (white crystals, m.p. 235°–237°C) (Lit. m.p. 232°C, J. Chem. Soc., 1941, 278). The 3.43 g sample of product exhibited no nitrile bands in the infrared spectrum but the infrared spectral band characteristic of the triazine structure was very strong at 6.6 $\mu$.

EXAMPLE II p-Tolunitrile (11.7 g, 0.10 mol) was added in small portions to 25 ml (42.5 g, 0.29 mol) of trifluoromethanesulfonic acid at 25°–30°C. After stirring overnight, the dark brown reaction mixture was poured on ice and neutralized with ammonium hydroxide. The insoluble precipitate was filtered off and washed with acetone to give 9.7 g of white solid. Recrystallization of this solid from toluene gave 7.5 g (64 percent yield) of 2,4,6-tri-p-tolyl-s-triazine (white crystals m.p. 282°–285°C) [Lit. m.p. 283°–285° C., J. Amer. Chem. Soc., 80, 1442 (1958)]. The infrared spectrum of the product exhibited the characteristic triazine bands at 6.6 $\mu$ and 12.45 $\mu$.

| Anal. | Calcd. for $C_{24}H_{21}N_3$: | C,82.02; H,6.02; N,11.95. |
|---|---|---|
| | Found: | C,81.73; H,5.84; N,11.80. |

EXAMPLE III m-Tolunitrile (11.7 g, 0.10 mol) was added dropwise to 30 ml (51 g, 0.35 mol) trifluoromethanesulfonic acid at 2°–8°C over a period of 20 minutes. The orange mixture was stirred at 25°C for 18 hours, poured on ice, neutralized with ammonium hydroxide and extracted with methylene chloride. The methylene chloride extract was dried and concentration provided 11.1 g of off-white solid. Recrystallization of this solid from n-hexane gave 9.2 g (78 percent yield) of 2,4,6-tri-m-tolyl-s-triazine (white fluffy crystals, m.p. 155°–155.5°C) [Lit, m.p. 151°–152° C. J. Amer. Chem. Soc., 80, 1442 (1958)]. The characteristic triazine band at 6.5 $\mu$ was present in the infrared spectrum of the product.

| Anal. | Calcd. for $C_{24}H_{21}N_3$: | C,82.02; H,6.02; N,11.95. |
|---|---|---|
| | Found: | C,81.93; H,6.16; N,11.62. |

EXAMPLE IV o-Tolunitrile (11.7 g, 0.10 mol) was added dropwise to 25 ml (42.5 g, 0.29 mol) trifluoromethanesulfonic acid at 0°–5°C. After storing at room temperature overnight, the reaction mixture was poured on ice, neutralized with ammonia and extracted with ether. After drying the ethereal extract, concentration provided 9.5 g of impure product. Recrystallization of the crude product from n-hexane provided 3.1 g of white crystals (m.p. 95°–115°C) and evaporation of the filtrate gave an additional 4.5 g which was recrystallized to give 0.40 g of 2,4,6-tri-o-tolyl-s-triazine (white crystals, m.p. 112°–114°C) (Lit. m.p. 110° C., J. Chem. Soc., 1941, 278). The characteristic triazine band at 6.5 $\mu$ was observed in the infrared spectrum of the product.

| Anal. | Calcd. for $C_{24}H_{21}N_3$: | C,82.02; H,6.02; N,11.95. |
|---|---|---|
| | Found: | C,81.96; H,5.95; N,11.82. |

EXAMPLE V p-Chlorobenzonitrile (6.8 g, 0.05 mol) was added in small portions to 25 ml (42.5 g, 0.29 mol) trifluoromethanesulfonic acid at 0°–10°C. The mixture became dark orange but was homogeneous; on removal of the ice bath, the mixture warmed to 30°–40°C. After stirring overnight, the mixture was poured on ice and a white flocculent precipitate formed. After neutralization with ammonium hydroxide, the precipitate formed. After neutralization with ammonium hydroxide, the precipitate was isolated by filtration and dried to give 10.2 g of 2,4,6-tri-p-chlorophenyl-s-triazine (white powdery crystals, m.p. 336°–339°C). Recrystallization from 400 ml toluene gave 3.9 g (36 percent yield) of 2,4,6-tri-p-chlorophenyl-s-triazine (asbestos-like crystals, m.p. 337°–340°C) (Lit. m.p. 335°C, J. Chem. Soc., 1941, 278). The infrared spectrum of the product exhibited a strong band at 6.6 $\mu$ characteristic of the triazine structure.

EXAMPLE VI p-Bromobenzonitrile (18.2 g, 0.10 mol) was added in small portions to 30 ml (51 g, 0.35 mol) trifluoromethanesulfonic acid at 0–10°C. The orange solution was homogeneous and was allowed to stand overnight at room temperature. The mixture was poured on ice and neutralized with ammonium hydroxide. A solid was removed by filtration and washed with 600 ml of a 50/50 mixture of methylene chloride/acetone to remove unreacted nitrile leaving 16.7 g of 2,4,6-tri-p-bromophenyl-s-triazine (white solid, m.p. 350–354°C) [Lit. m.p. 361–362°C, Chem. Abstr., 42, 2259 (1948)]. A 5 g portion of the product was recrystallized from boiling benzene to give white crystals of the same melting point, 350°–354°C. Infrared spectral analysis was consistent with the proposed triazine structure.

| Anal. | Calcd. for $C_{21}H_{12}Br_3N_3$: | C,46.18; H,2.20; N,7.70; Br,43.9. |
|---|---|---|
| | Found: | C,46.17; H,2.35; N,7.67; Br,41.91. |

EXAMPLE VII p-Methoxybenzonitrile (13.3 g, 0.10 mol) was added in small portions to 30 ml (51 g, 0.35 mol) trifluoromethanesulfonic acid at 0°–10°C with heat evolution and formation of a black color. The thickened mixture was allowed to stand overnight and was poured on ice followed by neutralization with ammonium hydroxide.

A yellow solid was isolated by filtration and air dried. Recrystallization of this yellow solid from N,N-dimethylformamide and water followed by washing the recrystallized material with ethanol and ether gave 7.8 g (59 percent yield) of 2,4,6-tris-p-methoxy-phenyl-s-triazine (m.p. 216.5°-219°C) [Lit. m.p. 214°-216°C, J. Org. Chem., 26, 2778 (1961)].

| Anal. | Calcd. for $C_{24}N_{21}N_3O_3$: | C,72.16; H,5.30; N,10.52. |
|---|---|---|
| | Found: | C,71.42; H,5.11; N,10.56. |

EXAMPLE VIII

Propionitrile (5.5 g, 0.10 mol) was added dropwise over a period of 20 minutes to 20 ml (34 g, 0.23 mol) trifluoromethanesulfonic acid at 2°-5°C. The mixture was allowed to warm to 23°C and stirred an additional 105 minutes. The yellow solution was poured on ice, made basic with ammonium hydroxide and extracted with ether. After drying, the ethereal extract was slowly distilled and 5.7 g of the residue was distilled in vacuo. A sample of 2,4,6-triethyl-s-triazine was collected at 60.6/3.0 mm [Lit. b.p., 125°/3 mm, f.p. 27, J. Org. Chem., 26, 2778 (1961)], and solidified on cooling to long needles. Infrared spectral analysis supported the structure assignment in that the strong band characteristic of the triazine structure was present at 6.5μ. The nuclear magnetic resonance spectrum was consistent with the proposed triazine structure.

| Anal. | Calcd. for $C_9H_{15}N_3$: | C,65.42; H,9.15; N,25.43; M.W. 165. |
|---|---|---|
| | Found: | C,65.64; H,9.11; N,25.42; M.W. 165*. |

*by osmometry

EXAMPLE IX n-Butyronitrile (6.9 g, 0.10 mol) was added dropwise to 20 ml (34 g, 0.23 mol) trifluoromethanesulfonic acid over a period of 5 minutes with the temperature rising to 21°C. After stirring overnight, the mixture was poured on ice and made basic with ammonium hydroxide. Extraction of the yellow solution with ether followed by drying and distillation of the ethereal extract gave 4.58 g of an oily residue. Distillation gave 1.99 g 2,4,6-tri-n-propyl-s-triazine (29 percent yield) collected at 71°-72°C (0.5 mm) [Lit. b.p. 71.5-72°/1 mm, Chem. Abstr., 58, 526 (1963)]. Gas chromatographic analysis of the distilled product indicated a 98 percent purity of the alkyl substituted triazine. Infrared and nuclear magnetic spectral analyses were consistent with the proposed 2,4,6-tri-n-propyl-s-triazine structure.

| Anal. | Calcd. for $C_{12}H_{21}N_3$: | C,69.52; H,10.21; N,20.27; M.W. 207 |
|---|---|---|
| | Found: | C,69.50; H,10.28; N,19.86; M.W. 200 |

*by osmometry

EXAMPLE X

Isobutyronitrile (20.73 g, 0.30 mol) was added dropwise to 50 ml (85 g, 0.58 mol) of cold trifluoromethanesulfonic acid over a period of 46 minutes with the temperature being maintained at 0°-9°C. The deep red solution was allowed to stir at room temperature overnight. The viscous reaction mixture was transferred to a 50 ml pear-shaped flask and distilled under vacuum. Trifluoromethanesulfonic acid (20.36 g) was collected at 28°-63°C (0.5 mm) with the pot temperature rising to 150°C. The pot residue, 48.7 g, was dissolved in chloroform and washed three times with water and the chloroform solution was made basic with ammonium hydroxide. The basic chloroform solution was washed with water and the organic phase was separated and dried over anhydrous magnesium sulfate. Concentration of the chloroform solution gave 22.18 g of a mobile red-brown oil. Distillation of 21.27 g provided a major fraction (13.12 g, 63 percent yield) of the desired triazine, 2,4,6-tri-isopropyl-s-triazine [b.p. 68°C (2.0 mm), $n_D^{20}$ 1.4590] [Lit. b.p. 98°/15 mm, J. Org. Chem., 26, 2778 (1961)], with only 1.65 g of pot residue. Gas chromatographic analysis indicated the major fraction to be 96 percent 2,4,6-tri-isopropyl-s-triazine.

EXAMPLE XI

Using the procedure described for Example IX, 0.10 mol isobutyronitrile was added to 20 ml (34 g, 0.23 mol) trifluoromethanesulfonic acid. Reaction workup and fractionation gave a 46 percent distilled yield of 2,4,6-tri-isopropyl-s-triazine, b.p. 77.5°–78°C/5.0 mm (99.4 percent purity by GLC). The infrared and nuclear magnetic resonance spectral analyses were consistent with the proposed 2,4,6-tri-isopropyl-s-triazine structure.

| Anal. | Calcd. for $C_{12}H_{21}N_3$: | C,69.52; H,10.21; N,20.27. |
|---|---|---|
| | Found: | C,69.45; H,9.98; N,19.50. |

A comparison of Examples X and XI demonstrates that an improved yield of 2,4,6-tri-isopropyl-s-triazine is obtained if trifluoromethanesulfonic acid is distilled from the reaction mixture prior to water quenching.

EXAMPLE XII

Chlorosulfonic acid has been shown to be an effective catalyst for the trimerization of benzonitrile, providing a 68 percent yield of 2,4,6-triphenyl-s-triazine (J. Chem. Soc., 1941, 278). However, as shown in the following example, chlorosulfonic acid is ineffective to trimerize isobutyronitrile.

Isobutyronitrile (20.73 g, 0.30 mol) was added slowly to 50 ml of chlorosulfonic acid over a period of about 45 minutes. The temperature increased to about 39°C before the reaction mixture was cooled. After all the isobutyronitrile had been added, the reaction mixture was stirred overnight at room temperature. Vacuum distillation was attempted but the mixture foamed so vigorously that the distillation was stopped and the reaction mixture was poured on ice. The mixture was made basic with ammonium hydroxide and extracted with ether. The ethereal extract was dried and concentrated to 1.9 g of residue which contained very little, if any, triazine according to infrared spectral analysis. The major product was isobutyramide.

Inasmuch as chlorosulfonic acid can be used to catalyze the trimerization of benzonitrile, yet was ineffective to catalyze the trimerization of isobutyronitrile, it was surprising to discover that trifluoromethanesulfonic acid could be used in the trimerization of both aromatic and aliphatic nitriles, as disclosed herein.

It will be evident to those skilled in the art that various modifications of this invention can be made, or followed, in the light of the foregoing disclosure and discussion, without departing from the spirit or scope thereof.

What is claimed is:

1. A process for the preparation of a substituted triazine of the formula

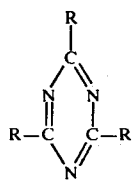

wherein R is a radical selected from the group consisting of alkyl, aryl and substituted aryl having from 2 to 9 carbon atoms per radical group, wherein said alkyl group contains an alpha-hydrogen, and wherein said substituted aryl is substituted with alkyl, halogen or alkoxy which comprises reacting a nitrile having the formula R-CN, wherein R is as defined above, under reaction conditions in the presence of trifluoromethanesulfonic acid.

2. The process of claim 1 wherein the molar ratio of said trifluoromethanesulfonic acid to said nitrile is in the range of 0.8:1 to 20:1.

3. The process of claim 1 wherein said nitrile is contacted with said trifluoromethanesulfonic acid at a temperature in the range of $-20°$ to $100°C$ for a time sufficient to effect trimerization.

4. The process of claim 1 wherein said R is aryl.

5. The process of claim 1 wherein said R is alkyl.

6. The process of claim 1 wherein said R is substituted aryl.

7. The process of claim 1 wherein said nitrile is benzonitrile.

8. The process of claim 1 wherein said nitrile is p-tolunitrile.

9. The process of claim 1 wherein said nitrile is n-tolunitrile.

10. The process of claim 1 wherein said nitrile is o-tolunitrile.

11. The process of claim 1 wherein said nitrile is p-chlorobenzonitrile.

12. The process of claim 1 wherein said nitrile is p-bromobenzonitrile.

13. The process of claim 1 wherein said nitrile is p-methoxybenzonitrile.

14. The process of claim 1 wherein said nitrile is propionitrile.

15. The process of claim 1 wherein said nitrile is n-butyronitrile.

16. The process of claim 1 wherein said nitrile is isobutyronitrile.

* * * * *